United States Patent
Prockop et al.

(10) Patent No.: US 9,675,665 B2
(45) Date of Patent: Jun. 13, 2017

(54) TREATMENT OF GUM DISEASES AND GUM DISORDERS WITH TSG-6 PROTEIN

(71) Applicants: Darwin J. Prockop, Philadephia, PA (US); Kathy K. H. Svoboda, Dallas, TX (US); Stacy Renay Beltran, McAllen, TX (US)

(72) Inventors: Darwin J. Prockop, Philadephia, PA (US); Kathy K. H. Svoboda, Dallas, TX (US); Stacy Renay Beltran, McAllen, TX (US)

(73) Assignee: The Texas A & M University System, College Station, TX (US)

( * ) Notice: Subject to any disclaimer, the term of this patent is extended or adjusted under 35 U.S.C. 154(b) by 0 days.

(21) Appl. No.: 15/102,776

(22) PCT Filed: Dec. 10, 2014

(86) PCT No.: PCT/US2014/069480
§ 371 (c)(1),
(2) Date: Jun. 8, 2016

(87) PCT Pub. No.: WO2015/094846
PCT Pub. Date: Jun. 25, 2015

(65) Prior Publication Data
US 2016/0310566 A1    Oct. 27, 2016

Related U.S. Application Data

(60) Provisional application No. 61/917,694, filed on Dec. 18, 2013.

(51) Int. Cl.
| | |
|---|---|
| A61P 17/02 | (2006.01) |
| A61P 1/02 | (2006.01) |
| A61P 41/00 | (2006.01) |
| A61K 38/17 | (2006.01) |
| C07K 14/47 | (2006.01) |
| C07K 14/525 | (2006.01) |

(52) U.S. Cl.
CPC ...... *A61K 38/1709* (2013.01); *C07K 14/4702* (2013.01); *C07K 14/525* (2013.01)

(58) Field of Classification Search
None
See application file for complete search history.

(56) References Cited

U.S. PATENT DOCUMENTS

| | | | |
|---|---|---|---|
| 5,674,074 A | 10/1997 | Angelo, Jr. | |
| 8,007,278 B2 | 8/2011 | Chao | |
| 8,088,405 B2 | 1/2012 | Uhrich | |
| 8,785,395 B2 * | 7/2014 | Prockop | A61K 9/0048 514/13.3 |

FOREIGN PATENT DOCUMENTS

| | | |
|---|---|---|
| WO | WO2007/101988 | 9/2007 |
| WO | WO2008/045345 | 4/2008 |

OTHER PUBLICATIONS

Beltran et al, (2015. J Periodontal. 86: 62-71).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Popova et al (2013; Biotechnol & Biotechnol. Eq. 27(3), 3754-3759).*
Yang, et al., PLOS One, vol. 9, Issue 6, pp. 1-7, e100285 (Jun. 2014).

* cited by examiner

*Primary Examiner* — Zachary Howard
(74) *Attorney, Agent, or Firm* — Raymond J. Lillie (57) ABSTRACT

A method of treating or preventing a gum disease or gum disorder or gum injury in a mammal by administering to the mammal at least one inflammation modulatory or anti-inflammatory protein or polypeptide, such as TSG-6 protein, or a biologically active fragment, derivative, or analogue thereof. Gum diseases or gum disorders or gum injuries that may be treated include periodontal gum disease, and gum wounds resulting from gum surgeries.

35 Claims, 7 Drawing Sheets

SEQUENCE LISTING

```
<160> NUMBER OF SEQ ID NOS: 2

<210> SEQ ID NO 1
<211> LENGTH: 277
<212> TYPE: PRT
<213> ORGANISM: Homo sapiens
<220> FEATURE:
<223> OTHER INFORMATION: TSG-6 protein

<400> SEQUENCE: 1

Met Ile Ile Leu Ile Tyr Leu Phe Leu Leu
1               5                   10

Leu Trp Glu Asp Thr Gln Gly Trp Gly Phe
                15                  20

Lys Asp Gly Ile Phe His Asn Ser Ile Trp
                25                  30

Leu Glu Arg Ala Ala Gly Val Tyr His Arg
                35                  40

Glu Ala Arg Ser Gly Lys Tyr Lys Leu Thr
                45                  50

Tyr Ala Glu Ala Lys Ala Val Cys Glu Phe
                55                  60

Glu Gly Gly His Leu Ala Thr Tyr Lys Gln
                65                  70

Leu Glu Ala Ala Arg Lys Ile Gly Phe His
                75                  80

Val Cys Ala Ala Gly Trp Met Ala Lys Gly
                85                  90

Arg Val Gly Tyr Pro Ile Val Lys Pro Gly
                95                  100

Pro Asn Cys Gly Phe Gly Lys Thr Gly Ile
                105                 110
```

```
Ile Asp Tyr Gly Ile Arg Leu Asn Arg Ser
            115                 120

Glu Arg Trp Asp Ala Tyr Cys Tyr Asn Pro
            125                 130

His Ala Lys Glu Cys Gly Gly Val Phe Thr
            135                 140

Asp Pro Lys Gln Ile Phe Lys Ser Pro Gly
            145                 150

Phe Pro Asn Glu Tyr Glu Asp Asn Gln Ile
            155                 160

Cys Tyr Trp His Ile Arg Leu Lys Tyr Gly
            165                 170

Gln Arg Ile His Leu Ser Phe Leu Asp Phe
            175                 180

Asp Leu Glu Asp Asp Pro Gly Cys Leu Ala
            185                 190

Asp Tyr Val Glu Ile Tyr Asp Ser Tyr Asp
            195                 200

Asp Val His Gly Phe Val Gly Arg Tyr Cys
            205                 210

Gly Asp Glu Leu Pro Asp Asp Ile Ile Ser
            215                 220

Thr Gly Asn Val Met Thr Leu Lys Phe Leu
            225                 230

Ser Asp Ala Ser Val Thr Ala Gly Gly Phe
            235                 240

Gln Ile Lys Tyr Val Ala Met Asp Pro Val
            245                 250

Ser Lys Ser Ser Gln Gly Lys Asn Thr Ser
            255                 260

Thr Thr Ser Thr Gly Asn Lys Asn Phe Leu
            265                 270

Ala Gly Arg Phe Ser His Leu
            275

<210> SEQ ID NO 2
<211> LENGTH: 10
<212> TYPE: PRT
<213> ORGANISM: Artificial sequence
<220> FEATURE:
<223> OTHER INFORMATION: Myc-tag

<400> SEQUENCE: 2

Glu Gln Lys Leu Ile Ser Glu Glu Asp Leu
1               5                   10
```

TREATMENT OF GUM DISEASES AND GUM DISORDERS WITH TSG-6 PROTEIN

This application is the national stage application of PCT Application No. PCT/US2014/069480, filed Dec. 10, 2014, which claims priority based on Provisional Application Ser. No. 61/917,694, filed Dec. 18, 2013, the contents of which are incorporated by reference in their entireties.

This application claims priority based on Provisional Application Ser. No. 61/917,694, filed Dec. 18, 2013, the contents of which are incorporated by reference in their entirety.

This application relates to the treatment of gum diseases and gum disorders and gum injuries in a mammal. More particularly, this application relates to the treatment or prevention of gum diseases and gum disorders and gum injuries, including gum wounds resulting from gum surgeries, in a mammal by administering to the mammal an inflammation modulatory or anti-inflammatory protein or polypeptide or biologically active fragment, derivative, or analogue thereof.

Gum diseases and disorders, such as gingivitis, periodontal gum disease or periodontitis, as well as gum injuries, including those resulting from gum surgeries, are the cause of a variety of symptoms including bacterial and/or viral infection, as well as gum inflammation, and gum bleeding. In addition, gum surgeries such as gingivectomies, gum flap surgeries, crown lengthenings, gum tissue grafts or gingivoplasties, result in gum wounds that may become inflamed or infected.

In treating gum diseases and disorders and gum injuries, such as, for example, those resulting from gum surgeries such as gingivectomies, gum tissue grafts or gigivoplasties, gum flap surgeries, and crown lengthening where a laceration induces an acute inflammatory response, as well as symptoms resulting from gum diseases and disorders such as gingivitis and periodontitis, tissue repair is of paramount importance.

For example, anti-inflammatory agents, and in particular corticosteroids, have been employed in attempts to effect wound healing in patients, and in particular, have been used in an attempt to effect the healing of wounds resulting from surgery. Wang, et al., *Am. J. Surg.*, Vol. 206, No. 3, pp. 410-417 (September 2013, Epub Jun. 4, 2013), however, have concluded that acute, high dose systemic corticosteroid use likely has no clinically significant effect on wound healing, and that chronic systemic administration of steroids may impair wound healing in certain individuals.

For example, corticosteroid complications include metabolic disorders such as hyperglycemia, adrenal insufficiency, and critical illness myopathy. (Cavaliere, et al., *Expert Opinion on Drug Safety*, Vol. 4, pgs. 1125-1133 (2005)). Also, dexamethasone, which is given often after surgery via intramuscular, intravenous, or oral administration to reduce inflammation, also suppresses the body's immune response. Side effects include stomach irritation, vomiting, headache, dizziness, insomnia, muscle weakness, depression, anxiety, vision problems, and in women, absent or irregular menstrual periods.

Applicants have discovered surprisingly that the administration of inflammation modulatory or anti-inflammatory proteins or polypeptides may improve the healing of gum wounds, such as gum wounds resulting from gum surgeries, as well as treat or prevent, other gum injuries, and gum diseases and gum disorders.

Thus, in accordance with an aspect of the present invention, there is provided a method of treating or preventing a gum disease or gum disorder or gum injury in a mammal. The method comprises administering to the mammal at least one inflammation modulatory or anti-inflammatory protein or polypeptide or biologically active fragment, derivative, or analogue thereof.

In a non-limiting embodiment, the at least one inflammation modulatory or anti-inflammatory protein or polypeptide is tumor necrosis factor-α stimulated gene 6 (TSG-6) protein or a biologically active fragment, derivative, or analogue thereof.

In a non-limiting embodiment, the TSG-6 protein is the "native" TSG-6 protein, which has 277 amino acid residues as shown hereinbelow.

```
MIILIYLFLL LWEDTQGWGF KDGIFHNSIW LERAAGVYHR

EARSGKYKLT YAEAKAVCEF EGGHLATYKQ LEAARKIGFH

VCAAGWMAKG RVGYPIVKPG PNCGFGKTGI IDYGIRLNRS

ERWDAYCYNP HAKECGGVFT DPKQIFKSPG FPNEYEDNQI

CYWHIRLKYG QRIHLSFLDF DLEDDPGCLA DYVEIYDSYD

DVHGFVGRYC GDELPDDIIS TGNVMTLKFL SDASVTAGGF

QIKYVAMDPV SKSSQGKNTS TTSTGNKNFL AGRFSHL
```

In another non-limiting embodiment, the at least one inflammation modulatory or anti-inflammatory protein or polypeptide is a fragment of TSG-6 protein known as a TSG-6-LINK protein, or a TSG-6 link module domain. In one non-limiting embodiment, the TSG-6 link module domain consists of amino acid residues 1 through 133 of the above-mentioned sequence (SEQ ID NO:1).

In another non-limiting embodiment, the TSG-6 link module domain consists of amino acid residues 1 through 98 of the above-mentioned sequence and is described in Day, et al., *Protein Expr. Purif.*, Vol. 8, No. 1, pgs. 1-16 (August 1996).

Additional biologically active fragments, derivatives, and analogues of TSG-6 protein are described in published PCT Application No. WO 2007/101988, Lee, et al., *J. Cell. Biol.*, Vol. 116, pgs. 545-557 (1992); Kohda, et al., *Cell*, Vol. 86, pgs. 767-775 (1996); Wisniewski, et al., *Cytokine and Growth Factor Reviews*, Vol. 8, pgs. 143-156 (1997); Bork, et al., *J. Mol. Biol.*, Vol. 231, pgs. 539-545 (1993); and Nagyeri, et al., *J. Biol. Chem.*, Vol. 286, pgs. 23559-23569 (2011), the contents of which are incorporated by reference.

In another non-limiting embodiment, the at least one inflammation modulatory or anti-inflammatory protein or polypeptide or a biologically active fragment, derivative, or analogue thereof, such as TSG-6 protein or a biologically active fragment, derivative, or analogue thereof, has a "His-tag" at the C-terminal thereof. The term "His-tag", as used herein, means that one or more histidine residues are bound to the C-terminal of the TSG-6 protein or biologically active fragment, derivative, or analogue thereof. In another non-limiting embodiment, the "His-tag" has ten amino acid residues at the C-terminal of the inflammation modulatory or anti-inflammatory protein or polypeptide, such as TSG-6 protein or a biologically active fragment, derivative, or analogue thereof. In another non-limiting embodiment, the "His-tag" has six histidine residues at the C-terminal of the inflammation modulatory or anti-inflammatory protein or polypeptide, such as TSG-6 protein or a biologically active fragment, derivative, or analogue thereof.

In a non-limiting embodiment, when the inflammation modulatory or anti-inflammatory protein or polypeptide, or biologically active fragment, derivative, or analogue thereof, includes a "His-tag", at the C-terminal thereof, the inflammation modulatory or anti-inflammatory protein or polypeptide, or biologically active fragment, derivative, or analogue thereof, may include a cleavage site that provides for cleavage of the "His-tag" from the inflammation modulatory or anti-inflammatory protein or polypeptide, or biologically active fragment, derivative, or analogue thereof, after the inflammation modulatory or anti-inflammatory polypeptide, or biologically active fragment, derivative, or analogue thereof is produced.

In another non-limiting embodiment, the at least one inflammation modulatory or anti-inflammatory protein or polypeptide, or a biologically active fragment, derivative, or analogue thereof, such as TSG-6 protein or a biologically active fragment, derivative, or analogue thereof, has a "Myc-tag" at the N-terminal or C-terminal thereof. The term "Myc-tag", as used herein, means a polypeptide tag derived from the c-myc gene product. In a non-limiting embodiment, the "Myc-tag" has the amino acid sequence EQKLISEEDL (SEQ ID NO:2).

In a non-limiting embodiment, when the inflammation modulatory or anti-inflammatory protein or polypeptide, or biologically active fragment, derivative, or analogue, thereof, includes a "Myc-tag" at the N-terminal or C-terminal thereof, the inflammation modulatory or anti-inflammatory protein or polypeptide, or biologically active fragment, derivative, or analogue thereof, may include a cleavage site that provides for cleavage of the "Myc-tag" from the inflammation modulatory or anti-inflammatory protein or polypeptide, or biologically active fragment, derivative, or analogue thereof, after the inflammation modulatory or anti-inflammatory polypeptide, or biologically active fragment, derivative, or analogue thereof is produced.

In yet another non-limiting embodiment, the at least one inflammation modulatory or anti-inflammatory protein or polypeptide, or a biologically active fragment, derivative, or analogue thereof, such as TSG-6 protein or a biologically active fragment, derivative, or analogue thereof, is bound, conjugated, or otherwise attached to at least one molecule, such as an adduct or congener, that enhances the biological activity and/or pharmacokinetic activity and/or residence time of the at least one inflammation modulatory or anti-inflammatory protein or polypeptide. In a non-limiting embodiment, such at least one molecule is polyethylene glycol, or PEG.

The at least one inflammation modulatory or anti-inflammatory protein or polypeptide may be made by techniques known to those skilled in the art. In a non-limiting embodiment, the at least one inflammation modulatory or anti-inflammatory protein or polypeptide may be prepared recombinantly by genetic engineering techniques known to those skilled in the art. In another non-limiting embodiment, the at least one inflammation modulatory or anti-inflammatory protein or polypeptide may be synthesized on an automatic peptide synthesizer.

In a non-limiting embodiment, the at least one inflammation modulatory or anti-inflammatory protein or polypeptide is administered systemically, such as by intravenous, intraarterial, or intraperitoneal administration, or the at least one inflammation modulatory or anti-inflammatory protein or polypeptide may be administered directly to the site of the gum disease or gum disorder or gum injury. In a non-limiting embodiment, the at least one inflammation modulatory or anti-inflammatory protein or polypeptide is administered intravenously. In another non-limiting embodiment, the at least one inflammation modulatory or anti-inflammatory protein or polypeptide is administered directly to the site of the gum disease or gum disorder or gum injury.

The at least one inflammation modulatory or anti-inflammatory protein or polypeptide may be administered to any mammal suffering from a gum disease or gum disorder or gum injury. In a non-limiting embodiment, the mammal is a primate, which includes human and non-human primates.

The at least one inflammation modulatory or anti-inflammatory protein or polypeptide may be administered in conjunction with an acceptable pharmaceutical carrier or excipient.

Suitable carriers and excipients include those that are compatible physiologically and biologically with the inflammation modulatory or anti-inflammatory protein or polypeptide and with the patient, such as phosphate buffered saline and other suitable carriers or excipients. Other pharmaceutical carriers that may be employed, either alone or in combination, include, but are not limited to, sterile water, alcohol, fats, waxes, and inert solids. Pharmaceutically acceptable adjuvants (e.g., buffering agent, dispersing agents) also may be incorporated into a pharmaceutical composition including the inflammation modulatory or anti-inflammatory protein or polypeptide. In general, compositions useful for parenteral administration are well known. (See, for example, Remington, *The Science and Practice of Pharmacy,* 22nd Edition, Allen, Jr., Ed., Pharmaceutical Press, Gurnee, Ill. (September 2012).

Gum diseases, gum disorders, and gum injuries which may be treated in accordance with the present invention include, but are not limited to, periodontal gum disease or periodontitis, gingivitis, and gingival wounds, including but not limited to, gingival wounds resulting from accidents, as well as from radiation exposure or radiation therapy, and from gum surgeries and other dental surgeries from which gum injuries may result. It is to be understood, however, that the scope of the present invention is not to be limited to the treatment or prevention of any particular gum disease or gum disorder or gum injury.

In a non-limiting embodiment, the gum disease or gum disorder that is treated is gingivitis. Gingivitis results from the formation of plaque and tartar on the teeth for an extended period of time. The longer that plaque and tartar remain on the teeth, the more harmful they become. The teeth and gums may become susceptible to bacterial infection. The bacteria infect the gums and cause an inflammation of the gums known as gingivitis. The gums become red and swollen, and may bleed easily. The at least one inflammation modulatory or anti-inflammatory protein or polypeptide, such as TSG-6 protein or a biologically active fragment, derivative, or analogue thereof may be administered to reduce or eliminate the redness, swelling or inflammation and/or gum bleeding caused by gingivitis.

In another non-limiting embodiment, the gum disease or gum disorder is periodontal gum disease or periodontitis.

When gingivitis is not treated, periodontal gum disease or periodontitis can develop. In periodontitis, the gums pull away from the teeth and form spaces or pockets that become infected. The immune system fights the infectious bacteria as plaque spreads and grows below the gum line. Bacterial toxins and the body's natural response to infection may start to break down the bone and connective tissue that hold the teeth in place. If not treated, the gums, bones and other tissue that support the teeth may be destroyed, and the teeth may become loose and have to be removed. The at least one inflammation modulatory or anti-inflammatory protein or polypeptide, such as TSG-6 protein or a biologically active fragment, derivative, or analogue thereof, may be administered to reduce or repair the gum damage caused by periodontal gum disease or periodontitis. In particular, the inflammation modulatory or anti-inflammatory protein or polypeptide, such as TSG-6 protein or a biologically active fragment, derivative, or analogue thereof may be administered to a patient to treat or repair the gum damage caused by periodontal gum disease or periodontitis before the bone and connective tissue that holds the teeth in place are affected.

Gum surgeries or other dental surgeries from which gum injuries may result include, but are not limited to, dental implant surgeries, crown lengthening, cosmetic dental surgeries, gingivectomies, gum flap surgeries, gum tissue grafts, or gingivoplasties, correction of mucogingival defects, alone or in combination with bone grafts such as jaw bone grafts and maxillary bone grafts, and other surgeries such as alveolar ridge augmentation and resections of soft and hard tissues of the periodontium.

In a non-limiting embodiment, the gum surgery is a gingivectomy.

A gingivectomy attempts to remove the soft tissue wall of the periodontal pocket by an external bevel incision that leaves a cut surface exposed to the oral cavity. (Genco, et al., *Contemporary Periodontics*, St. Louis, The C.V. Mosby Company, pg. 729 (1990)). As shown by Goldman, *Oral Surgery, Oral Medicine, and Oral Pathology*, Vol. 4, pgs. 1135-1157 (1951), the primary incision is begun as far apically to the pocket depth as possible to achieve a long bevel. The gingiva is excised down to the base of the pocket to include part of the epithelial attachment, leaving a portion of the connective tissue of the gingival corium above the alveolar crest. (Waite, *J. Clin. Periodontology*, Vol. 2, pgs. 241-249 (1975)). The knife then is brought deeper into the interproximal areas to sever the papillae. The initial incision is made with a surgical knife or blade, extending interproximally as far as possible. After this is accomplished, the tissue generally is loosened and can be removed easily using a scaler or curette Gingivectomies may be performed in combination with many periodontal procedures, including the elimination of diseased tissue or other resective procedures such as crown lengthening. The at least one inflammation modulatory or anti-inflammatory protein or polypeptide, such as TSG-6 protein or a biologically active fragment, derivative, or analogue thereof, may be administered in order to treat or prevent any gum inflammation and/or injury that may result from the gingivectomy.

In another non-limiting embodiment, the gum surgery is a gum flap surgery. Gum flap surgery may be performed if gum inflammation and deep gum pockets remain after deep cleaning and medications are given to treat periodontal gum disease or periodontitis. Gum flap surgery is performed to remove tartar deposits in deep gum pockets or to reduce periodontal gum pockets. The surgery involves lifting back the gums and removing the tartar. The gums then are sutured back in place such that the gum tissue fits snugly around the tooth. The at least one inflammation modulatory or anti-inflammatory protein or polypeptide, such as TSG-6 protein or a biologically active fragment, derivative, or analogue thereof, may be administered in order to treat or prevent any gum inflammation and/or injury that may result from such gum flap surgery.

In another non-limiting embodiment, the gum surgery or dental surgery is a gum tissue graft or gingivoplasty, which may be performed alone or in combination with a jaw bone graft or a maxillary bone graft. Such grafts may help regenerate gum tissue or bone tissue lost to periodontal gum disease or periodontitis.

In gum tissue grafts or gingivoplasties, a synthetic material or tissue taken from another area of the mouth is used to cover exposed tooth roots. In some cases, guided tissue regeneration and/or bone grafts also may be performed. In bone grafting, natural or synthetic bone is placed in an area of bone loss in the jaw bone or maxillary bone in order to promote bone growth. Guided tissue regeneration also may be performed in combination with bone or gum tissue grafts, wherein a small piece of mesh-like material is inserted between the bone and gum tissue in order to keep the gum tissue from growing into the area where bone should be, thus allowing the bone and connective tissue to regrow with the gum tissue.

The at least one inflammation modulatory or anti-inflammatory protein or polypeptide, such as TSG-6 protein or a biologically active fragment, derivative, or analogue thereof thus may be administered prevent or reduce the effects of any injury to the gums that may result from a graft of gum tissue, performed alone or in combination with guided tissue regeneration or bone grafting.

The at least one inflammation modulatory or anti-inflammatory protein or polypeptide, or biologically active fragment, derivative, or analogue thereof, is administered in an amount effective to treat or prevent a gum disease or a gum disorder or a gum injury in a mammal. In a non-limiting embodiment, when administered systemically, such as by intravenous, intra-arterial, or intraperitoneal administration, the at least one inflammation modulatory or anti-inflammatory protein or polypeptide, or biologically active fragment, derivative, or analogue thereof, is administered in a total amount of from about 5 micrograms to about 500 milligrams. In another non-limiting embodiment, when administered systemically, the at least one inflammation modulatory or anti-inflammatory protein or polypeptide, or biologically active fragment, derivative, or analogue thereof, is administered in a total amount of from about 100 milligrams to about 500 milligrams. In another non-limiting embodiment, when the inflammation modulatory or anti-inflammatory protein or polypeptide, or biologically active fragment, derivative, or analogue thereof is administered directly to the site of the gum disease or gum disorder or gum injury, the at least one inflammation modulatory or anti-inflammatory protein or polypeptide, or biologically active fragment, derivative, or analogue thereof, is administered in an amount of from about 0.1 microgram to about 1 milligram. The exact amount of inflammation modulatory or anti-inflammatory protein or polypeptide or fragment, derivative, or analogue thereof to be administered is dependent on a variety of factors, including, but not limited to, the age, weight, and sex of the patient, the type of gum disease or gum disorder or gum injury to be treated, and the extent and severity thereof.

In another non-limiting embodiment, the at least one inflammation modulatory or anti-inflammatory protein or polypeptide, or biologically active fragment, derivative, or analogue thereof, can be administered up to 10 years after the onset of the gum disease or gum disorder or within 6 hours of the infliction of the gum injury. In yet another non-limiting embodiment, the at least one inflammation modulatory or anti-inflammatory protein or polypeptide, or biologically active fragment, derivative, or analogue thereof is administered within a few seconds after the infliction of the gum injury, such as, for example, a surgical wound.

Although the scope of these embodiments is not intended to be limited to any theoretical reasoning, it is believed that when the at least one inflammation modulatory or anti-inflammatory protein or polypeptide, or biologically active fragment, derivative, or analogue thereof, is administered within 10 years of the onset of the gum disease or gum disorder or within 6 hours of the infliction of the gum injury, the at least one inflammation modulatory or anti-inflammatory protein or polypeptide (e.g., TSG-6), or biologically active fragment, derivative, or analogue thereof acts as a modulator of the inflammation that results from the gum disease or gum disorder or gum injury, thereby treating or alleviating the adverse effects of the gum disease or gum disorder or gum injury.

In a non-limiting embodiment, the at least one inflammation modulatory or anti-inflammatory protein or polypeptide (e.g., TSG-6), or biologically active fragment, derivative, or analogue thereof may be administered in combination with other agents for treating or preventing gum diseases or gum disorders, such as, for example, antibiotics and antiseptic mouthwashes.

BRIEF DESCRIPTION OF THE DRAWINGS

The invention now will be described with respect to the drawings, wherein:

FIG. 1. (A) Pre-surgical measurements (PCPUNC15 perio probe); (B) Surgical transection of the gingiva (Miltex stainless steel disposable #12 scalpel); (C) Injecting 2 µg TSG-6/PBS solution (3/10 cc insulin syringe U-100 29 g ½ needle with rubber stopper 1 mm from tip end).

FIG. 3. (A) 24 hrs post-surgery. Group 1 (rh TSG-6), Group 2 (PBS), Group 3 (Control), respectively; (B) 48 hrs post-surgery. Group 1 (rh TSG-6), Group 2 (PBS), Group 3 (Control), respectively; (C) Mean score with respect to time by group.

FIG. 6. ELISAs. (A) MPO assay. Units of MPO are $$\frac{ng}{\mu g}$$

of protein; (B) IL-1β. Units of IL-1β are $$\frac{pg}{\mu g}$$

of protein; (C) IL-6. Units or IL-6 are $$\frac{pg}{\mu g}$$

of protein.

EXAMPLE

The invention now will be described with respect to the following example; however, the scope of the present invention is not intended to be limited thereby.

Inflammation is the body's normal protective response to an injury, irritation, or surgery. Acute inflammation refers to a response that is abrupt in onset and of short duration. If the cause of the initial injury is not completely eliminated, acute inflammation gradually will give way to chronic inflammation, though no definitive time sequence.

The acute inflammatory response has three major components: hemodynamic changes, alterations in the permeability of vessels, and changes in the location and concentration of white blood cells. Weissman, *Cell Biology of Inflammation*, New York, Elsevier Science, Ltd., pg 736 (1980). Injury to tissues triggers a specific acute response that involves an exudative reaction of fluid, serum proteins, and leukocytes that leave the blood stream to enter the area of injury, often causing symptoms of pain, heat, redness and swelling. The events of the vascular response to injury, which also include release of polypeptide cytokines and growth factors from peripheral blood monocytes, aim to localize and eliminate the injurious agents and remove damaged tissue components so the body can begin to heal.

Human adult stem/progenitor cells from bone marrow, referred to as mesenchymal stem cells or multipotent mesenchymal stromal cells (hMSCs), have been at the forefront of modern research. Throughout their course of study, evolving data has led to the development of various hypotheses regarding their role in wound repair. Among their therapeutic factors, MSCs express the multipotent anti-inflammatory protein tumor necrosis factor (TNF)-α-stimulated gene 6 protein in response to tissue injury. (Prockop, et al., *Molecular Therapy: The Journal of the American Society of Gene Therapy*, Vol. 20, pgs. 14-20 (2012)).

TNF-α-stimulated gene 6 protein, or TSG-6, is a hyaluronan (HA)-binding protein that since has been implicated in the negative regulation of inflammatory tissue destruction. TSG-6 DNA was isolated originally from a cDNA library prepared from TNF-α-treated human fibroblasts. (Lee, et al., *J. Cell. Biol.*, vol 116, pgs. 545-557 (1992)). It is secreted by various cells, such as fibroblasts, upon stimulation by the proinflammatory cytokines tumor necrosis factor or Interleukin-1 (IL-1). The rapid upregulation of TSG-6 in the presence of the proinflammatory cytokines tumor necrosis factor, or TNF, and IL-1 is consistent with its involvement in inflammatory processes. (Milner, et al., *J. Cell Sci.*, Vol. 116, pgs. 1863-1873 (2003)). This association was confirmed by the detection of TSG-6 protein in synovial fluids of patients with a variety of conditions including rheumatoid arthritis, osteoarthritis, Sjogren's syndrome, polyarthritic gout, and osteomyelitis. (Wisniewski, et al., *J. Immunol.*, Vol 151, pgs. 6593-6601 (1993)). There are no studies to date that evaluate the properties of TSG-6 on gum diseases or gum disorders such as gingival inflammation. Therefore, this study tests the effects of recombinant human (rh) TSG-6 on early gingival wound healing in an animal model.

Materials and Methods

The experimental model used in this study involved the creation of an acute inflammatory lesion; localized to the maxillary and mandibular gingival tissue in a rat model. The hyaluronan (HA)-binding protein, rhTSG-6 (purchased from R & D Systems), was used to test its anti-inflammatory effects following injury. This protocol was submitted for review and approved by the Institutional Animal Care and Use Committee at Baylor College of Dentistry—a member of The Texas A&M University System.

Study Animals

One hundred twenty adult male (DOB: Dec. 14, 2012), Sprague Dawley rats (Harlan Laboratories), each weighing approximately 400 grams, were used in this study in an attempt to minimize interspecies variance. All animals were housed in individual polycarbonate cages and provided with standard rat chow pellets and water ad libitum. Rats were separated into three groups (experimental, sham, control) and were numbered for identification purposes via tail markings. All animals were given a 7-day acclimation period with a 12-hour light/12-hour dark cycle. Rats were monitored daily throughout the experimental period. General anesthesia was induced by administering Ketamine (0.08 mL/100 g) and Xylazine (0.04 mL/100 g) intramuscularly. Following onset of anesthesia, the animals were weighed and placed on a surgical table. An aseptic surgical technique was utilized. All protocols for anesthesia, postoperative care, and necropsy of the animal subject were approved by the Institute of Animal Care and Use Committee prior to commencement of study.

Surgical Procedures

Figure 1A:
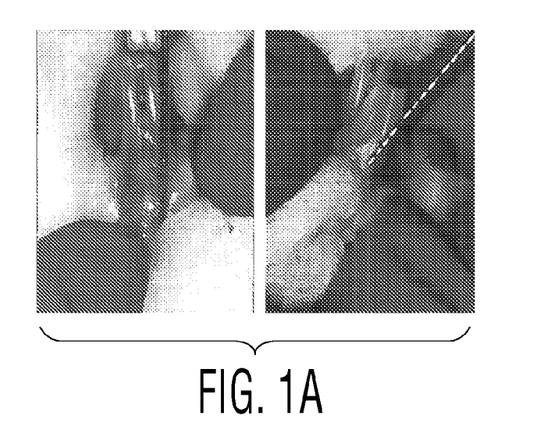
Figure 1B:
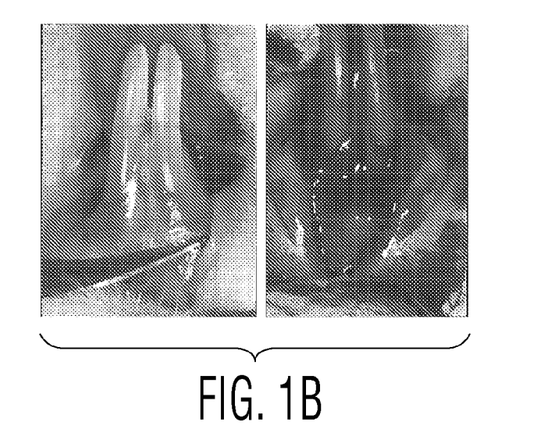
Figure 1C:
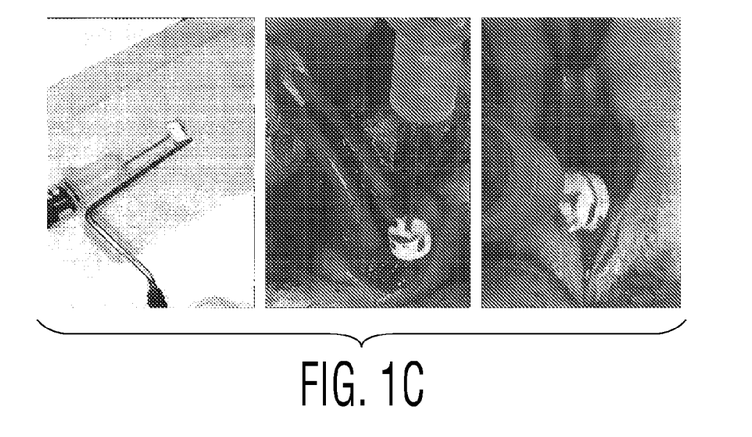

Ketamine (0.08 mL/100 g) and Xylazine (0.04 mL/100 g) were combined for use as a general anesthetic and given as an intraperitoneal injection using a 1 ml syringe 23-25 gauge ⅝ inch needle. All rats were weighed prior to surgical procedures. Animals were numbered and divided among three groups:

Group 1: Experimental (40 animals)-gingivectomy+TSG-6
Group 2: Sham (40 animals)-gingivectomy+PBS
Group 3: Control (40 animals)-gingivectomy Using a Miltex stainless steel disposable #12 scalpel, under 3.5× magnification via dental loops, a standardized gingival wound was produced in one hundred and twenty animals. The wound consisted of a gingivectomy performed on the mandibular and maxillary anterior marginal and attached gingiva, removing a triangular piece of tissue between the central mandibular and maxillary incisors. Incisions were performed at an angle of 45° and at 2 mm from each tooth surface. All measurements were made with a Hu-Fredy PCPUNC15 perio probe (FIG. 1A). The scalpel was inserted in the keratinized tissue so as to obtain a complete surgical transection of the gingiva (FIG. 1B). A Gracey 11-12 curette was utilized to remove excised gingival tissue. Immediately after tissue removal, 2 µg recombinant human TSG-6 (rhTSG-6) in 5 µL of PBS solution was injected into the gingival tissue approximating the surgical wound in forty experimental rats (Group 1). The depth of needle insertion, for delivery of the solution, was standardized using a rubber stopper 1 mm from the needle point (FIG. 1C). Injections were made with a 3/10 cc insulin syringe 29 gauge ½ needle. The same volume of PBS solution was injected into the gingival tissue in forty additional rats (Group 2). The forty control animals (Group 3) were not injected following gingivectomy. All animals (Groups 1, 2 & 3) were assessed at 4 different time points:

1-2 hrs: 10 animals
6-8 hrs: 10 animals
24 hrs: 10 animals
48 hrs: 10 animals

Intraoral photographs were taken of all animals at time of sacrifice.

Specimen Recovery Procedures

At the time points allocated (1-2, 6-8, 24, and 48 hrs) post-surgery, all animals per specified group were euthanized. Euthanasia was accomplished via a $CO_2$ chamber, for ease of handling, prior to decapitation. Weights were recorded for all animals before decapitation.

At the time of sacrifice, blood was collected into test tubes from each animal. Samples were placed on ice into 15 ml polypropylene tubes with 0.5M EDTA. Blood was spun down at 3,000 rpm for 20 minutes. Plasma was collected and frozen at $-20°$ C. until further analysis of inflammatory markers could be assessed via ELISA assays.

Random allocation performed prior to surgery determined the distribution of maxillary and mandibular gingival tissue per method of analysis—histology or myeloperoxidase assay (MPO).

Figure 2:
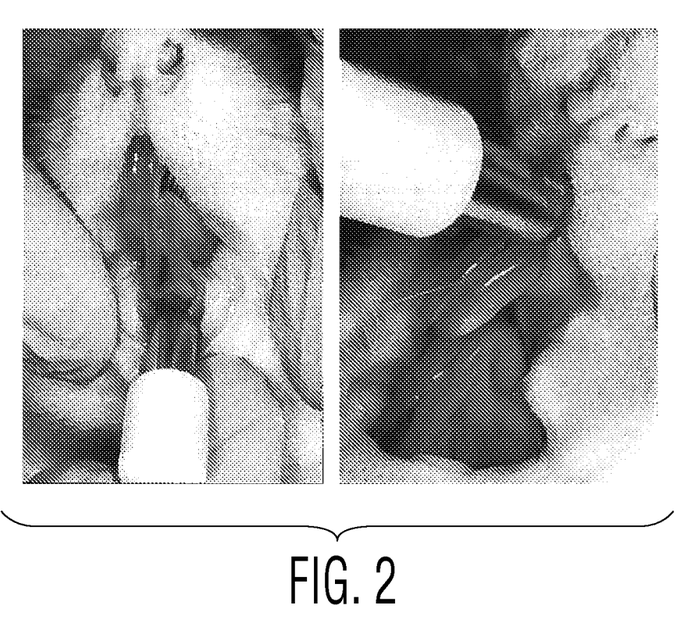
FIG. 2. Specimen collection (4 mm Tru-Punch sterile disposable biopsy punch).

Tissue specimens were obtained from the incisional border at the site of injury with a 4 mm Tru-Punch sterile disposable biopsy punch (Sklarcorp) (FIG. 2). Maxillary and mandibular specimens were separated, according to a randomization chart, and placed into bottles labeled for histopathology, containing 4% paraformaldehyde, or MPO assay. All specimens were frozen until termination of all surgical procedures.

Gingival Surface Evaluation and Clinical Outcome Analysis

At the time of sacrifice, gingival wounds in the mandibular arch were photographed utilizing a Digital SLR camera with a DG 105 mm f/2.8 Macro EX Sigma Lens at a distance of approximately 12 inches from the specimen. Four photographs from each group, from each time point, were selected for clinical evaluation. Each photograph then was assigned a number corresponding to the degree of inflammation observed by 18 blinded volunteers comprised of periodontists and periodontal residents. All volunteers were given an initial description and photograph corresponding to the severity of inflammation to be observed. Subjects were asked to determine the severity of gingival inflammation using criteria presented to each subject before the survey. Severity was determined on a 3-point—(1) mild, (2) moderate, and (3) severe basis. The assessment criteria provided, is as follows:

1=mild inflammation or with slight changes in color and texture but not in all portions of marginal or papillary gingiva. Non-bleeding.
2=moderate, bright surface inflammation, erythema, edema and/or hypertrophy of marginal or papillary gingiva.
3=severe inflammation; erythema, edema and/or gingival hypertrophy of the unit or spontaneous bleeding, papillary, congestion or ulceration.

Histological Processing/ELISAs

Individual specimens were prepared for histological analysis using standard procedures for biopsy specimens. Tissue samples were fixed in 4% Paraformaldehyde at $4°$ C. After dehydration, specimens were immersed in paraffin and processed for sectioning. Paraffin embedded specimens were sectioned at 5 microns thickness. Slides were stained with hematoxylin and eosin (H&E) and studied under a light microscope.

Tissue for ELISA testing was homogenized in 500 ul TPER with HALT+EDTA as a protease inhibitor. Specimens were spun down for 20 minutes at $4°$ C. 3000 rpm. Supernatant was then pulled off and frozen at $-20$ C until used for ELISA analysis.

Statistical Analysis

Before the initiation of this study, the sample size was determined to be 10 animals per treatment group per time point based on a power test with $\alpha=0.05$. A Difference Z-test was performed on pre-surgical weight (PreSW) versus post-surgical weight (PostSW). Weights were tested separately and plotted using a boxplot. Simultaneous paired t-tests were performed to determine between which groups exhibited a significant difference. To analyze the presence of significant differences for each protein and enzyme at each point of time between each subgroup a Kruskal-Wallis Rank Sum Test for Two-Sided One-Way ANOVA was performed. For all tests the level of marginal significance was $0.05 \leq \alpha 0.1$, and the level of significance $\alpha < 0.05$. The survey data was analyzed using Kruskal-Wallis Rank Sum Test. A plot with associated p-values at each time category was produced. Because the data is nonparametric, and n<4, the Mann-Whitney two sample comparison test was not performed.

Results

Clinical Assessment

Figure 3A:
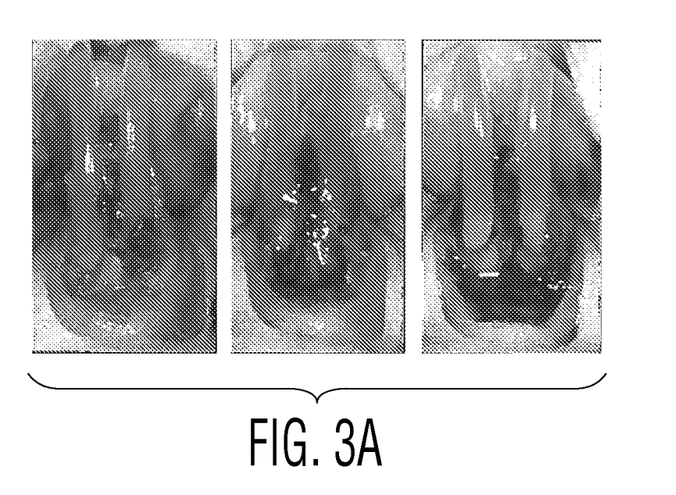
Figure 3B:
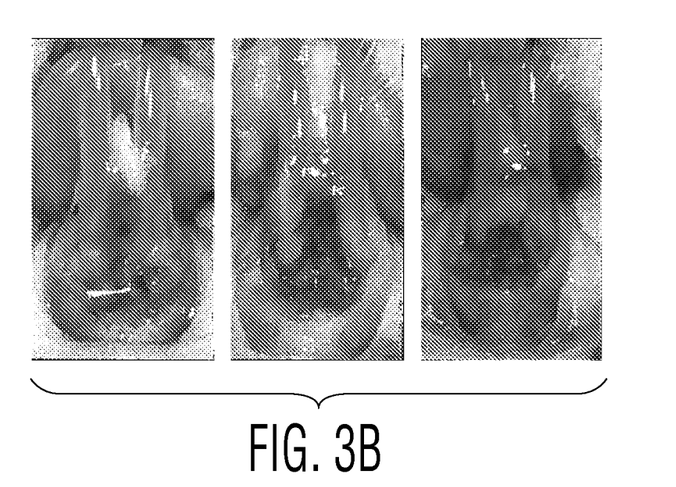
Figure 3C:
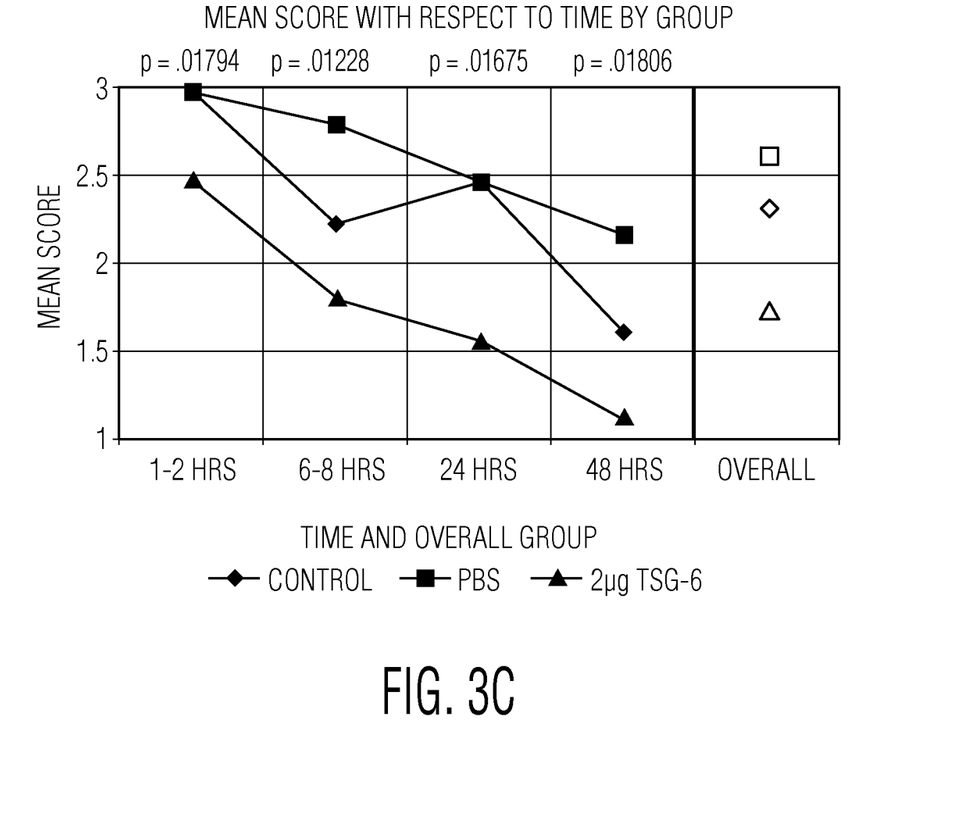

From the time of gingivectomy until the time of sacrifice (hours to days), no signs of infection or adverse healing were noted. Clinical evaluation at the time of sacrifice for the 1-2 hour group revealed erythematous and edematous gingival tissue. Tissues continued to appear inflamed and swollen at 6-8 hours post-surgery. By 24 hours, gingiva appeared moderately erythematous. An early wound covered with a blood clot was generally present. At 48 hours, gingival tissue appeared generally pink and non-bleeding. Results of the survey data are presented on FIG. 3. The means of each group at each time point were plotted. Overall, the data indicates conclusively that at each time point, Group 1 (TSG-6) showed lower inflammation as a result of visual analysis by the subjects at 6-8 hrs. (p=0.01228), 24 hrs. (p=0.01675), and 48 hrs. (p=0.01806). There was a significant difference between Group 1(TSG-6) and Group 2 (PBS) (p<0.001) and a significant difference between Group 1 and Group 3 (Control) (p=0.016). Additionally, Group 2 showed the highest levels of inflammation at all points. Unexpectedly, Group 3 showed an unusual score increase between 6-8 hrs and 24 hrs.

Weights

Figure 4:
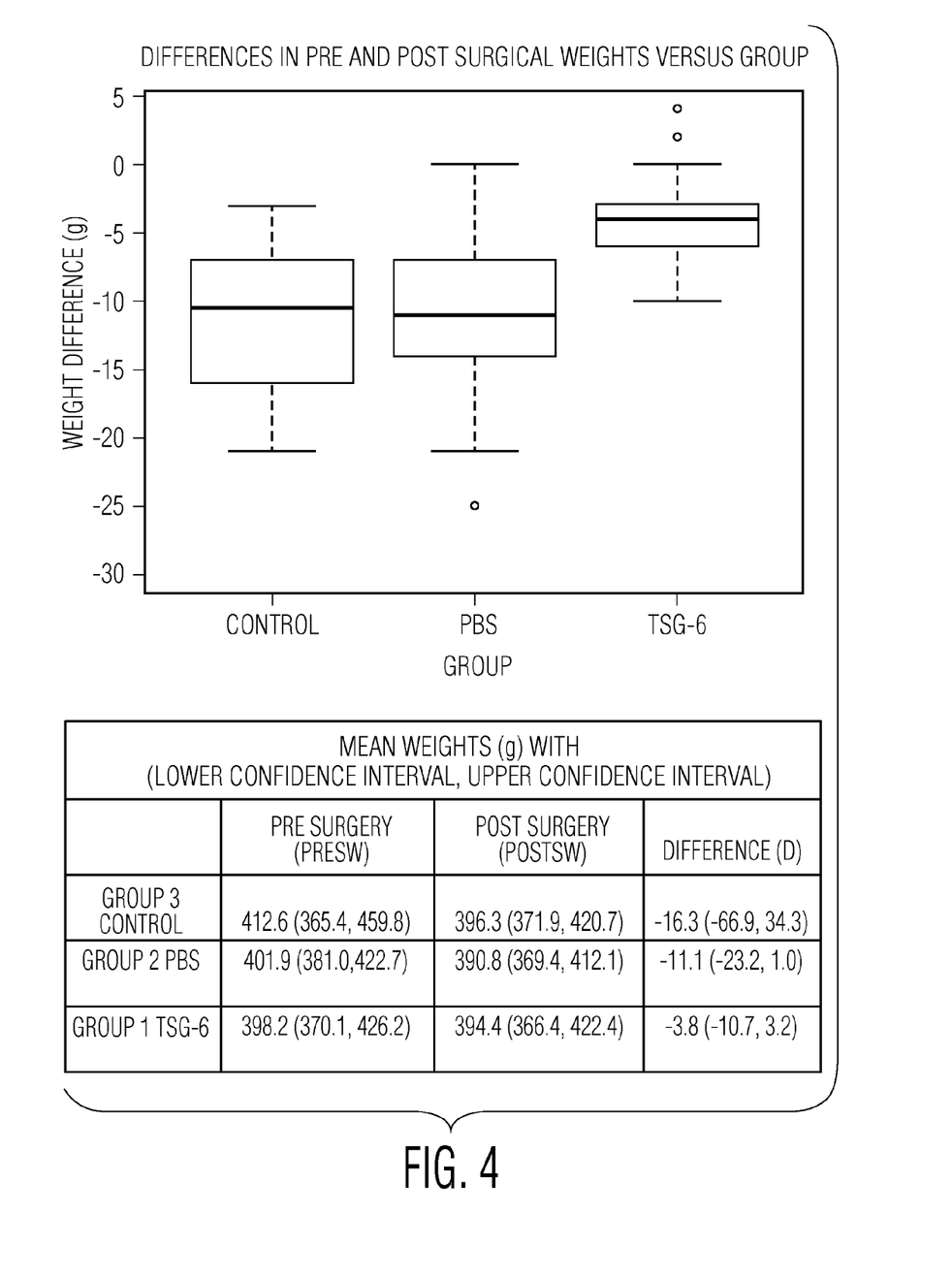
FIG. 4. Box plot comparison. Differences in Pre-Surgical and Post-surgical Weights versus Group.

All animals were weighed at baseline and at time of sacrifice. The mean weights for the 24-hr and 48-hr group were tabulated. The difference from the mean pre-surgical to post-surgical weights for the 24-hr Group 1 (TSG-6), Group 2 (PBS) and Group 3 (Control) were 1.8, 8.9, and 10.8 grams, respectively. The difference from the mean pre-surgical to post-surgical weights for the 48-hr Group 1 (TSG-6), Group 2 (PBS) and Group 3 (control) were 5.7, 12.1, and 11.8 grams, respectively. The mean, with a 95% confidence interval, was tabulated for all animals and presented in FIG. 4. It is evident that overall, post-surgical weights were lower than pre-surgical weights. Differences in mean weights were −3.8, −11.1, and −16.3 for Group 1, 2 and 3, respectively. A box plot comparison of the differences in pre-surgical and post-surgical weights versus group illustrates that the Group 1 (TSG-6) showed a lower loss in weight (calculated as |PostSW−PreSW|) than the other two groups (FIG. 4). Additionally, simultaneous paired t-tests were performed to determine between which groups exhibited a significant difference post-surgically. There was a significant difference between Group 1 (TSG-6) and Group 2 (PBS) (p<0.001) and a significant difference between Group 1 and Group 3 (Control) (p=0.016). There was no significant difference between Groups 2 & 3.

Histology

Figure 5:
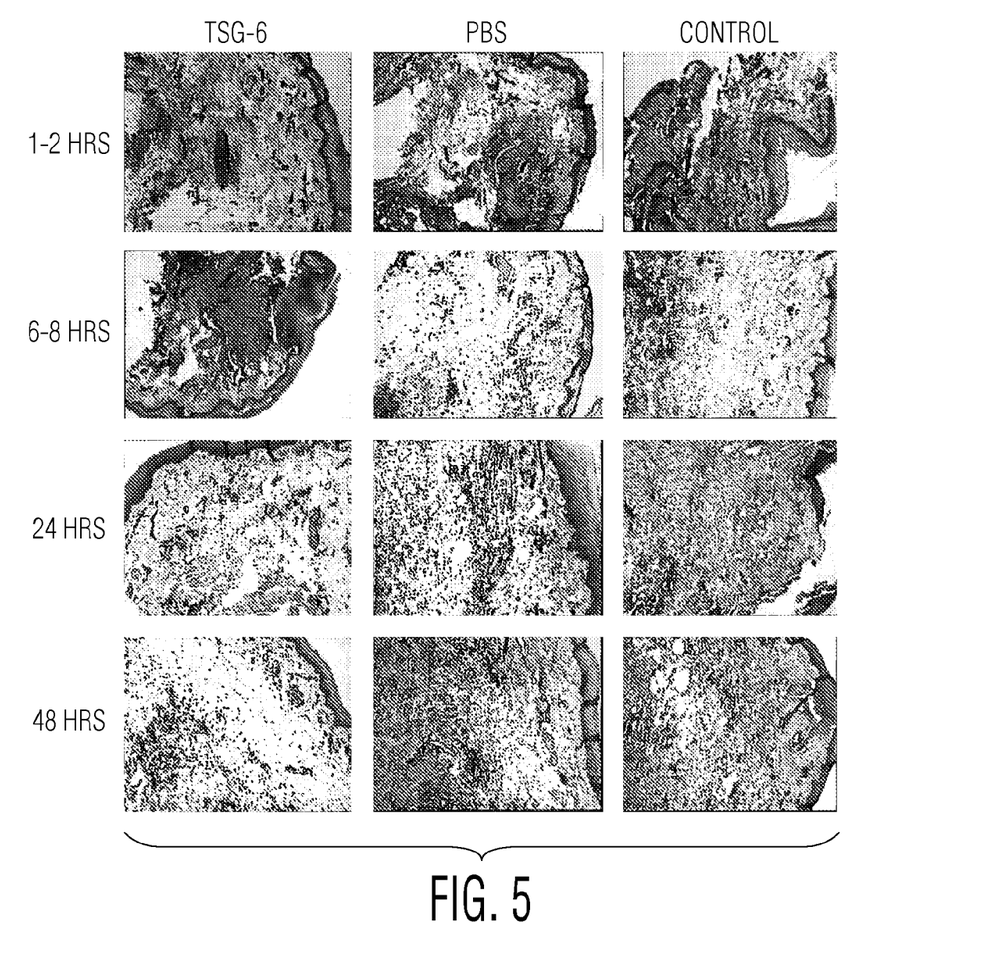
FIG. 5. Histology. H & E stain of specimens per treatment group per time point.

Three tissue specimens per treatment group and time point were analyzed. Specimens chosen for histologic analysis were obtained from the same animals utilized in the visual assessment examination. H & E stain showed similar amounts of cellular infiltrate at 1-2 hours post-surgery. Cellular infiltrate increased over the subsequent hours analyzed. Generally, Groups 2 & 3 (PBS & Control) showed markedly more infiltrate compared to Group 1 (TSG-6) at 6-8, 24, and 48 hours (FIG. 5).

ELISAs

Figure 6A:
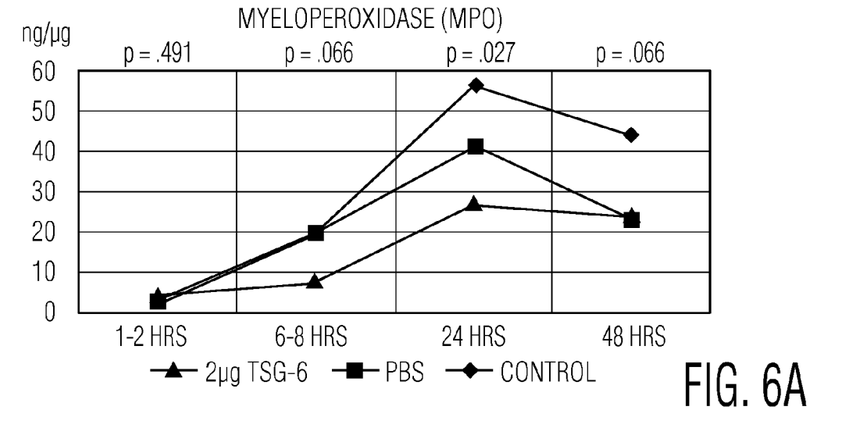

Myeloperoxidase (MPO) assay revealed an increase in MPO levels between 1-2 hours and 24 hours, but a slight decrease between 24 and 48 hours. All MPO levels showed similar values at the 1-2 hour time point, and thus showed no significant difference. There were marginal significant differences noted at 6-8 and 48 hours (p=0.66) and a significant difference between the three groups at 24 hours (p=0.027). Group 1 showed a 43.8% reduction in MPO levels at 24 hours when compared to Group 3. The group treated with TSG-6 had the lowest levels between 6-8 and 24 hours. The control group showed the highest level of MPO for 24 to 48 hours. For each data point n=3 (FIG. 6).

Figure 6B:
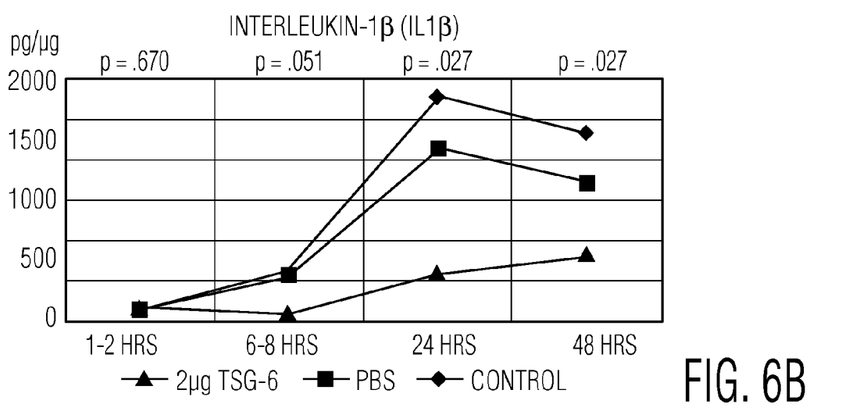

Blood samples for Interleukin 1β (IL-1β) were analyzed via ELISA; however, levels of IL-1β were not detectable, indicating no systemic involvement. Tissue samples therefore were utilized to assess cytokine levels. Data revealed an increase in IL-1β between 1-2 and 24 hours, but a decrease between 24 and 48 hours except Group 1. The test showed no significant difference at the initial point, 1-2 hours (p=0.670), but there were marginal significant differences at 6-8 hours (p=0.051), and a significant difference between the three groups at 24 and 48 hours (p=0.027). Group 1 showed a 68.0% reduction in levels of IL-1β at 24 hours when compared to Group 3. Overall, the group treated with the TSG-6 has the lowest levels between 6-8 hours, 24 hours, and 48 hours. For each data point n=3 (FIG. 6).

Figure 6C:
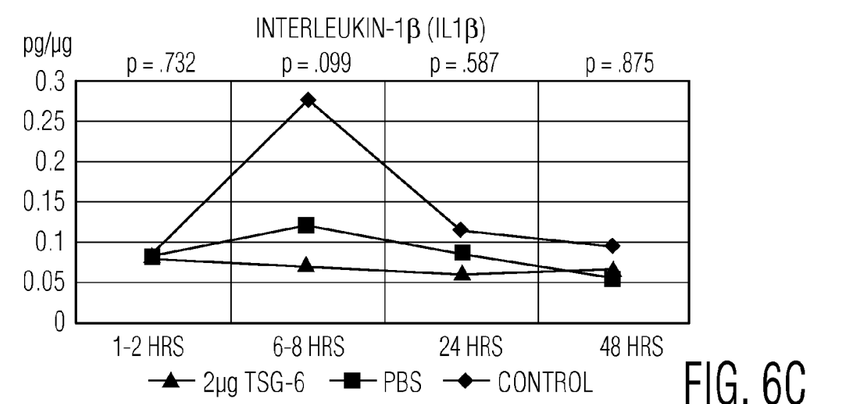

Interleukin 6 (IL-6) was elevated between 1-2 hours and 6-8 hours, but there was a decrease in IL-6 levels between 6-8 hours and 24 hours and between 24 hours and 48 hours. Overall, the group treated with TSG-6 had the lowest levels between 6-8 hours and 24 hours. The control group showed the highest level of IL-6 for 6-8, 24, and 48 hours. There was a marginal significant difference at 6-8 hours (p=0.099) (FIG. 6). Group 1 showed a 50.9% reduction in levels of IL-6 at 6-8 hours when compared to Group 3.

Discussion

Healing of periodontal tissue after surgical treatment has long been a subject of interest. In the current study, the anti-inflammatory effects of tumor necrosis factor-α-stimulated gene 6 protein (TSG-6) was evaluated following injection into an acute gingival wound in Sprague-Dawley rats. Within the limits of this study, injection of 2 µg TSG-6 was found to accelerate wound healing by reducing inflammatory cell infiltrate and reducing cytokines IL-1β and IL-6. Significant differences were seen at 6-8, 24, and 48 hours, as observed clinically and microscopically.

Similar findings have been reported when 2 µg TSG-6 were injected into the anterior chamber of rats' eyes following mechanical injury. (Oh, et al., *Proc. Nat. Acad. Sci.*, Vol. 107, pgs. 16875-16880 (2010)). In addition, TSG-6 reduced corneal inflammation and opacity in a dose-dependent manner. In transgenic mice, its anti-inflammatory effects were observed when an overexpression of the gene decreased inflammation and joint destruction following induced arthritis. Mindrescu, et al., *Arthritis and Rheumatism*, Vol. 46, pgs. 2453-2464 (2002)). Likewise, TSG-6 was associated with a lower density of macrophages and infiltrating leukocytes, reduced levels of pro-inflammatory cytokines, and increased levels of anti-inflammatory cytokines following infusion of MSCs into the CNS of post traumatic brain injuries in rats. (Zhang, et al., *Journal of Neuroinflammation*, Vol. 110, pg. 106 (2013)). The anti-inflammatory activity of TSG-6 has been attributed to its ability to suppress neutrophil migration into the site of inflammation and inhibit components in the inflammatory network of proteases. (Milner, et al., *Biochem. Soc. Transactions*, Vol. 34, pgs. 446-450 (2006)).

The present study showed that intragingival injection of rhTSG-6 decreased the infiltration of neutrophils, pro-inflammatory cytokines, and reduced clinical signs of inflammation following gingival transection within the first 2 days following surgery.

All rats were weighed pre-surgically and post-surgically immediately prior to decapitation. Weight differences were analyzed and compared between 24 and 48 hour groups. Simultaneous t-tests were performed to determine between which groups existed a significant difference. All animals injected with TSG-6 showed less weight loss compared to animals not injected with TSG-6. Animals not injected with the protein evidently ate less or stopped eating after surgery, indicating that in addition to decreasing inflammation, TSG-6 may have some influence on pain perception. Pain is a subjective sensation. From the site of injury, impulses travel to the central nervous system and to higher centers of the brain responsible for determining the magnitude of pain. Vasodilation and increases in vascular permeability at the site of injury result in heat, redness, and swelling; while exuded fluid produces pressure on sensory nerve endings. Pain in an animal is often inferred from the absence of normal behaviors such as alertness, mobility, groomed coat, or a good appetite. (*Recognition on Alleviation of Pain in Laboratory Animals*, Washington, D.C., National Academy of Sciences (2009)). One can speculate that the animals that received TSG-6 were experiencing less pain/discomfort, primarily associated with a reduced state of inflammation, and subsequently were able to maintain their eating habits compared to control animals.

Within hours of injury, inflammatory cells (predominantly neutrophils and monocytes) populate the clot. These cells cleanse the wound of microorganisms and necrotic tissue via phagocytosis and release of enzymes and toxic oxygen products. (Polimeni, et al., *Periodontology*, Vol. 41, pgs. 30-47 (2006)). Histologically, cellular infiltrate was less pronounced in specimens obtained from animals receiving rhTSG-6 injections, most notably at 6-8, 24, and 48 hours.

In this study, quantification of neutrophils was assessed both morphologically and biochemically. Myeloperoxidase (MPO), released from the granules of neutrophils and monocytes in response to the activation of leukocytes plays an important role in several inflammatory conditions. MPO is a lysosomal protein that produces hypochlorous acid (HOCl) from hydrogen peroxide and chloride anion. The neutrophil uses the hypochlorous acid, which is cytotoxic, to kill bacteria and other pathogens. Hypochlorous acid is an extremely powerful oxidant that rapidly attacks a wide range of target molecules. For a quantitative measure of neutrophil infiltration, gingival specimens were assayed for MPO concentration. Because TSG-6 has been shown to suppress neutrophil infiltration directly, assessment of MPO concentration was chosen for evaluation, as opposed to C-reactive protein (CRP). CRP is an acute phase protein synthesized by the liver in response to factors released predominately by macrophages and fat cells. As anticipated, TSG-6 had significantly decreased levels of MPO in the gingiva. This finding correlates with our histological observations; reduced cellular infiltrate in specimens injected with TSG-6.

A similar pattern was observed in data obtained by assays of the tissue for expression of proinflammatory cytokines. The expression of proinflammatory cytokines, IL-1β and IL-6, were reduced markedly by TSG-6 treatment. Similar findings in expression of cytokine levels were seen when TSG-6 was injected into the eyes of rats following injury. (Oh, 2010). Neutrophils, monocytes, and other cells produce innate immune cytokines such as IL-1, IL-6, and TNF-α after being summoned to the site of injury by chemokines. In this study, levels of TNF-α (data not shown) were undetectable. These findings parallel those of Oh et al and colleagues. In their study, TNF-α was not detected in treated or untreated corneas by ELISA or real-time PCR analysis. (Oh, 2010). TNF-α, while known to stimulate the acute phase reaction, is produced chiefly by activated macrophages. It is a potent chemoattractant for neutrophils and promotes the expression of adhesion molecules on endothelial cells. Inconsistencies with other data sets in this study remain unclear.

In addition, it is of interest that intragingival injection of TSG-6 had no effect on plasma cytokine levels as determined by ELISA, indicating intragingival injection of 2 μg rhTSG-6 had no systemic involvement. TSG-6 acted locally on tissues to down regulate inflammatory mediators. This is in contrast to earlier findings by Getting, et al. and colleagues in which as little as 1 μg TSG-6 was administered at a site remote from the inflammatory environment. Reductions in neutrophil influx and inhibitions of IL-1β were observed. (Getting, et al., *J. Biol. Chem.*, Vol. 277, pgs. 51068-51076 (2002)). Their findings suggest that TSG-6 does not need to be given locally to the site of inflammation but, rather, acts via the circulation.

The mechanism of action observed by the anti-inflammatory effects of TSG-6 is not well understood. In recent studies, however, Inter-a-inhibitor, an abundant plasma protein with anti-proteolytic activity, consisting of three polypeptides: two heavy chains and one light chain, has been shown to bind to hyaluronan molecules via covalent bonds; a reaction thought to be mediated by TSG-6. TSG-6 has been shown to be bound tightly to the hyaluronan-linked heavy chains. This complex has been implicated in stabilizing extracellular matrix by cross-linking hyaluronan molecules and protecting hyaluronan against fragmentation by reactive oxygen species, enhancing tissue repair. (Fries, *Acta Biochemica Polonica*, Vol. 50, pgs. 735-742 (2003)). Though the anti-inflammatory properties are likely to be attributable to more than one mechanism, as witnessed by its diverse biologic properties, including the downregulation of plasmin activity, inhibition of neutrophil migration, as well as anti-resorptive properties, much research is needed to clarify its physiologic role in wound healing among humans. (Mahoney, et al., *J. Biol. Chem.*, Vol. 280, pgs. 27044-27055 (2005); Szanto, et al., *Arthritis and Rheumatism*, Vol. 50, pgs. 3012-3022 (2004); Mahoney, et al., *J. Biol. Chem.*, Vol., 283, pgs. 25952-25962 (2008)).

Inflammation, though protective in nature, can cause cellular damage if not controlled. For instance, neutrophil granules contain more than 20 proteolytic enzymes; of these, elastase, collagenase, and gelatinase have the greatest potential to act as mediators of tissue destruction. (Trowbridge, et al., *Inflammation: A Review of the Process*, Quintessence Publishing, pg. 236 (1997)). These enzymes are able to attack extracellular matrix. In addition, hypochlorous acid, induced by myeloperoxidase, can inactivate key proteinase inhibitors while activating latent neutrophil proteinases. Lysosomal enzymes also become susceptible to host tissue. Leakage of lysosomal enzymes during phagocytosis or cell death may result in tissue damage. Reverse endocytosis and regurgitation during feeding (phagocytosis) may also permit release of these lytic enzymes into surrounding tissues. (Trowbridge, 1997). Damage to host tissue is almost inevitable. Efforts to control or limit the inflammatory burden are paramount in restoring the body to health.

Resective surgeries in non-inflammed tissue are common practices in the field of periodontics for treatment of altered passive eruption, overgrown gingiva, crown lengthening, gingival recontouring, gingival flap retraction for access to impacted teeth/roots, or for implant placement. Extension of the incision as well as tissue manipulation and length of surgery could affect the extent of swelling. Post-operative discomfort resulting from swelling and pain following different surgical strategies is an area of great interest. Attention has been focused on non-steroidal anti-inflammatory drugs (NSAIDs) and corticosteroid therapy administered by diverse routes (orally, IM, IV, topically) before or after surgery. Side effects of corticosteroids include, but are not limited to hyperglycemia, adrenal insufficiency, and reductions in immune response. Efforts to find new anti-inflammatory agents that reduce post-operative discomfort are well underway.

TSG-6 may decrease pain as well as inflammation. Placing animals into feeding chambers and/or analyzing pain pathways and alternations thereof could provide significant insight into the molecular mechanisms of TSG-6. Replications of these experiments with larger treatment groups would be of great value. This study demonstrates that a single intragingival injection of TSG-6 reduced local post-operative inflammation, limiting destruction of the tissue by the normal but excessive inflammatory response to a sterile injury.

CONCLUSION

This is the first in vivo study to compare the clinical and histological effects of TSG-6 on gingival inflammation in an animal model. Within the limits of the study, injection of 2 µg rhTSG-6 reduced post-operative inflammation significantly by decreasing levels of the pro-inflammatory cytokines 1L1 β (68%) and IL-6 (50.9%), neutrophil infiltration (43.8%), erythema, and bleeding within the first few hours and days after injury. TSG-6 offers substantial promise for patients undergoing gingival resective surgery.

The disclosures of all patents and publications (including published patent applications), depository accession numbers, and database accession numbers are hereby incorporated by reference to the same extent as if each patent, publication, depository accession number, and database accession number were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A method of treating or preventing a gum disease or gum disorder or gum injury in a mammal comprising:
   administering to said mammal, prior to the loss of bone that holds the teeth in place, tumor necrosis factor-α stimulated gene 6 (TSG-6) protein or a biologically active fragment, or derivative comprising a fragment thereof, wherein said TSG-6 protein or biologically active fragment, or derivative comprising a fragment, thereof is administered in an amount effective to treat or prevent said gum disease, gum disorder, or gum injury in said mammal.

2. The method of claim 1 wherein said TSG-6 protein or biologically active fragment, or derivative comprising a fragment thereof is administered systemically.

3. The method of claim 2 wherein said TSG-6 protein or biologically active fragment, or derivative comprising a fragment thereof is administered intravenously.

4. The method of claim 3 wherein said TSG-6 protein or biologically active fragment, or derivative comprising a fragment thereof is administered in an amount of from about 5 micrograms to about 500 milligrams.

5. The method of claim 4 wherein said TSG-6 protein or biologically active fragment, or derivative comprising a fragment thereof is administered in an amount of from about 100 milligrams to about 500 milligrams.

6. The method of claim 1 wherein said TSG-6 protein or biologically active fragment, or derivative comprising a fragment thereof is administered directly to the site of the gum disease, gum disorder, or gum injury.

7. The method of claim 6 wherein said TSG-6 protein or biologically active fragment, or derivative comprising a fragment thereof is administered in an amount of from about 0.1 microgram to about 1 milligram.

8. The method of claim 1 wherein said mammal is a primate.

9. The method of claim 8 wherein said primate is a human.

10. The method of claim 1 wherein said gum disease, gum disorder, or gum injury is a gingival wound.

11. The method of claim 10 wherein said TSG-6 protein or biologically active fragment, or derivative comprising a fragment thereof is administered within 6 hours of the occurrence of said gingival wound.

12. The method of claim 10 wherein said gingival wound results from a gum surgery.

13. The method of claim 12 wherein said gum surgery is a gingvectomy.

14. The method of claim 12 wherein said gum surgery is a gum flap surgery.

15. The method of claim 12 wherein said gum surgery is a gum tissue graft.

16. The method of claim 1 wherein said gum disease, gum disorder, or gum injury is periodontal gum disease.

17. The method of claim 1 wherein said gum disease, gum disorder, or gum injury is gingivitis.

18. The method of claim 1 wherein said TSG-6 protein or biologically active fragment, or derivative comprising a fragment thereof has the sequence (SEQ ID NO: 1).

19. The method of claim 1 wherein said TSG-6 protein or biologically active fragment, or derivative comprising a fragment thereof consists of amino acid residues 1 through 133 of (SEQ ID NO: 1).

20. The method of claim 1 wherein said TSG-6 protein or biologically active fragment, or derivative comprising a fragment thereof consists of amino acid residues 1 through 98 of (SEQ ID NO: 1).

21. A method of treating or preventing a gum disease, gum disorder, or gum injury in a mammal, comprising:

administering directly to the gum of said mammal tumor necrosis factor-αstimulated gene 6 (TSG-6) protein, or a biologically active fragment, or derivative comprising a fragment thereof, wherein said TSG-6 protein or biologically active fragment, or derivative comprising a fragment thereof is administered in an amount effective to treat or prevent said gum disease, gum disorder, or gum injury in said mammal.

22. The method of claim 21 wherein said TSG-6 protein or biologically active fragment, or derivative comprising a fragment thereof is administered in an amount of from about 0.1 microgram to about 1 milligram.

23. The method of claim 21 wherein said mammal is a primate.

24. The method of claim 23 wherein said primate is a human.

25. The method of claim 21 wherein said gum disease, gum disorder, or gum injury is a gingival wound.

26. The method of claim 25 wherein said TSG-6 protein or biologically active fragment, or derivative comprising a fragment thereof is administered to the gum of said mammal within 6 hours of the occurrence of said gingival wound.

27. The method of claim 25 wherein said gingival wound results from a gum surgery.

28. The method of claim 27 wherein said gum surgery is a gingivectomy.

29. The method of claim 27 wherein said gum surgery is a gum flap surgery.

30. The method of claim 27 wherein said gum surgery is a gum tissue graft.

31. The method of claim 21 wherein said gum disease, gum disorder, or gum injury is periodontal gum disease.

32. The method of claim 21 wherein said gum disease, gum disorder, or gum injury is gingivitis.

33. The method of claim 21 wherein said TSG-6 protein or biologically active fragment, or derivative comprising a fragment thereof has the sequence (SEQ ID NO: 1).

34. The method of claim 21 wherein said TSG-6 protein or biologically active fragment, or derivative comprising a fragment thereof consists of amino acid residues 1 through 133 of (SEQ ID NO: 1).

35. The method of claim 21 wherein said TSG-6 protein or biologically active fragment, or derivative comprising a fragment thereof consists of amino acid residues 1 through 98 of (SEQ ID NO: 1).

* * * * *